United States Patent
Pan et al.

(10) Patent No.: US 11,822,629 B2
(45) Date of Patent: Nov. 21, 2023

(54) METHOD AND APPARATUS FOR GENERATING DIGITAL IDENTITY AND STORAGE MEDIUM

(71) Applicant: BGI SHENZHEN CO., LIMITED, Guangdong (CN)

(72) Inventors: Guangming Pan, Guangdong (CN); Meng Yang, Guangdong (CN); Hongde Zhao, Guangdong (CN); Qiang Tang, Guangdong (CN); Tong Zhou, Guangdong (CN); Hang Li, Guangdong (CN); Huaping Li, Guangdong (CN)

(73) Assignee: BGI SHENZHEN CO., LIMITED, Guangdong (CN)

( * ) Notice: Subject to any disclaimer, the term of this patent is extended or adjusted under 35 U.S.C. 154(b) by 358 days.

(21) Appl. No.: 17/122,361

(22) Filed: Dec. 15, 2020

(65) Prior Publication Data

US 2021/0150005 A1    May 20, 2021

Related U.S. Application Data

(63) Continuation of application No. PCT/CN2018/091880, filed on Jun. 19, 2018.

(51) Int. Cl.
*G06F 21/31* (2013.01)
*G16B 50/00* (2019.01)

(52) U.S. Cl.
CPC ............. *G06F 21/31* (2013.01); *G16B 50/00* (2019.02)

(58) Field of Classification Search
None
See application file for complete search history.

(56) References Cited

U.S. PATENT DOCUMENTS 11,468,194 B2 * 10/2022 Huang ................. G06F 21/6254
11,539,516 B2 * 12/2022 Grass ...................... G16B 25/00
(Continued)

FOREIGN PATENT DOCUMENTS

| CN | 101526975 A | 9/2009 |
| CN | 106520982 A | 3/2017 |

(Continued)

OTHER PUBLICATIONS

International Search Report dated Mar. 27, 2019 for corresponding International Application No. PCT/CN2018/091880, Jun. 19, 2018.
(Continued)

*Primary Examiner* — James R Turchen
(74) *Attorney, Agent, or Firm* — David D. Brush; Westman, Champlin & Koehler, P.A.

(57) ABSTRACT

A method for generating a digital identity is provided, including: extracting a first preset number of short tandem repeat STRs and relevant information of each STR from whole genome data; generating a single STR digital code corresponding to each STR according to the relevant information of each STR, to obtain a plurality of single STR digital codes; performing sequence transformation on each single STR digital code with a preset rule, and generating a target STR digital code according to the single STR digital code after the sequence transformation; generating summary information of the target STR digital code, and determining the summary information as summary information of the STR to which the target STR digital code belongs; and determining the summary information of the STR as the generated digital identity.

9 Claims, 4 Drawing Sheets

(56) References Cited

U.S. PATENT DOCUMENTS

| | | | |
|---|---|---|---|
| 2002/0129251 A1* | 9/2002 | Itakura | H04L 9/3247 |
| | | | 713/176 |
| 2003/0086591 A1 | 5/2003 | Simon | |
| 2012/0153018 A1 | 6/2012 | Nietfeld | |
| 2013/0103951 A1* | 4/2013 | Klevan | G06F 21/34 |
| | | | 713/186 |
| 2014/0081665 A1* | 3/2014 | Holmes | G06F 21/32 |
| | | | 705/3 |
| 2015/0254912 A1* | 9/2015 | Weisman | H04L 9/0866 |
| | | | 705/325 |
| 2016/0117492 A1* | 4/2016 | Chabanne | H04L 9/3231 |
| | | | 726/19 |

FOREIGN PATENT DOCUMENTS

| | | | | |
|---|---|---|---|---|
| CN | 106906300 A | 6/2017 | | |
| WO | 2013028699 A2 | 2/2013 | | |
| WO | WO-2019081145 A1 * | 5/2019 | | G16B 20/00 |

OTHER PUBLICATIONS

Written Opinion of the International Searching Authority dated Mar. 27, 2019 for corresponding International Application No. PCT/CN2018/091880, filed Jun. 19, 2018.
European Search Report dated Jan. 11, 2022 for related European Application No. 18923623.5.

* cited by examiner

FIG. 4

```
marking the position information of each STR in the whole
genome data with a first number of bits, and determining the
marked first number of bits as a first digital code, the position         S501
information comprising chromosome number, a starting site
and a fragment length of the STR
```

```
marking the repeated base pair sequence information of each
STR with a second number of bits, and determining the                     S502
marked second number of bits as a second digital code
```

```
marking the number of repetitions for the repeated base pairs
sequence with a third number of bits, and determining the                 S503
marked third number of bits as a third digit code
```

```
performing concatenation processing on the first digital code,
the second digital code, and the third digital code of each               S504
STR, and determining the concatenated digital code as the
single STR digital code corresponding to each STR
```

FIG. 5

METHOD AND APPARATUS FOR GENERATING DIGITAL IDENTITY AND STORAGE MEDIUM

CROSS-REFERENCE TO RELATED APPLICATION

This application is a continuation application of International Application No. PCT/CN2018/091880, filed with the China National Intellectual Property Administration on Jun. 19, 2018, the entire contents of which are incorporated herein by reference.

TECHNICAL FIELD

Embodiments of the present disclosure relate to a field of computer technology, and particularly to a method and apparatus for generating a digital identity, and a non-transitory computer-readable storage medium.

BACKGROUND

Traditional digital identities may be divided into two categories. One is the digital identity that needs to correspond to the physical identity with real names, which is referred to as entity digital identity for short. The most typical applications include resident ID cards issued by government, personal digital certificates issued by banks, and legal person digital certificates. The other is the virtual digital identity that does not need to correspond to the physical identity, which is referred to as virtual digital identity for short. Common applications include user names for a variety of network services, etc.

The corresponding relationship between the entity digital identity and the physical identity is as follows: the issuance and management of the entity digital identity require a real physical identity for associated authentication, that is, each digital identity corresponds to one real physical identity, and the physical identity is generally identified through the biometric information of a natural person (such as, facial features or fingerprint features).

The offline entity personal biometric information identification technology that the entity digital identity in related technologies relies on is relatively weak. Relying on biometric information identification technology to generate digital identities has the following problems: there is no guarantee for the uniqueness of biometrics without repetition in the digital identity application based on facial features identification technology (such as ID number), since the biometrics are of higher reproducibility (easier to perform a plastic surgery) and the accuracy of manual or machine facial identification cannot reach 100%. Thus the expression effect of digital identity is not good.

SUMMARY

In embodiments of the present disclosure, a method for generating a digital identity is provided. The method includes: extracting a first preset number of short tandem repeat STRs and relevant information of each STR from whole genome data; generating a single STR digital code corresponding to each STR according to the relevant information of each STR, to obtain a plurality of single STR digital codes; performing sequence transformation on each single STR digital code with a preset rule, and generating a target STR digital code according to the single STR digital code after the sequence transformation; generating summary information of the target STR digital code, and determining the summary information as summary information of the STR to which the target STR digital code belongs; and determining the summary information of the STR as the generated digital identity.

In embodiments of the present disclosure, an apparatus for generating a digital identity is provided. The apparatus includes: a processor; and a memory configured to store executable program codes, wherein the processor is configured to execute programs corresponding to the executable program codes by reading the executable program codes stored in the memory, so as to perform: extracting a first preset number of short tandem repeat STRs and relevant information of each STR from whole genome data; generating a single STR digital code corresponding to each STR according to the relevant information of each STR, to obtain a plurality of single STR digital codes; performing sequence transformation on each single STR digital code with a preset rule, and generating a target STR digital code according to the single STR digital code after the sequence transformation; generating summary information of the target STR digital code, and determining the summary information as summary information of the STR to which the target STR digital code belongs; determining the summary information of the STR as the generated digital identity.

In embodiments of the present disclosure, a non-transitory computer-readable storage medium having instructions stored therein is provided. When the instructions are executed by a processor of an electronic device, the processor performs a method for generating the digital identity. The method includes: extracting a first preset number of short tandem repeat STRs and relevant information of each STR from whole genome data; generating a single STR digital code corresponding to each STR according to the relevant information of each STR, to obtain a plurality of single STR digital codes; performing sequence transformation on each single STR digital code with a preset rule, and generating a target STR digital code according to the single STR digital code after the sequence transformation; generating summary information of the target STR digital code, and determining the summary information as summary information of the STR to which the target STR digital code belongs; and determining the summary information of the STR as the generated digital identity.

Other effects of the above-mentioned alternative manners will be described below in conjunction with the detailed embodiments.

BRIEF DESCRIPTION OF THE DRAWINGS

The above and/or additional aspects and advantages of the present application will become obvious and easy to understand from the following description of the embodiments in conjunction with the accompanying drawings, in which:

FIG. 4 is a schematic diagram of index information in an embodiment of the present application;

FIG. 5 is a schematic flowchart of a method for generating a digital identity according to another embodiment of the present application;

DETAILED DESCRIPTION

Figures 1, 2:
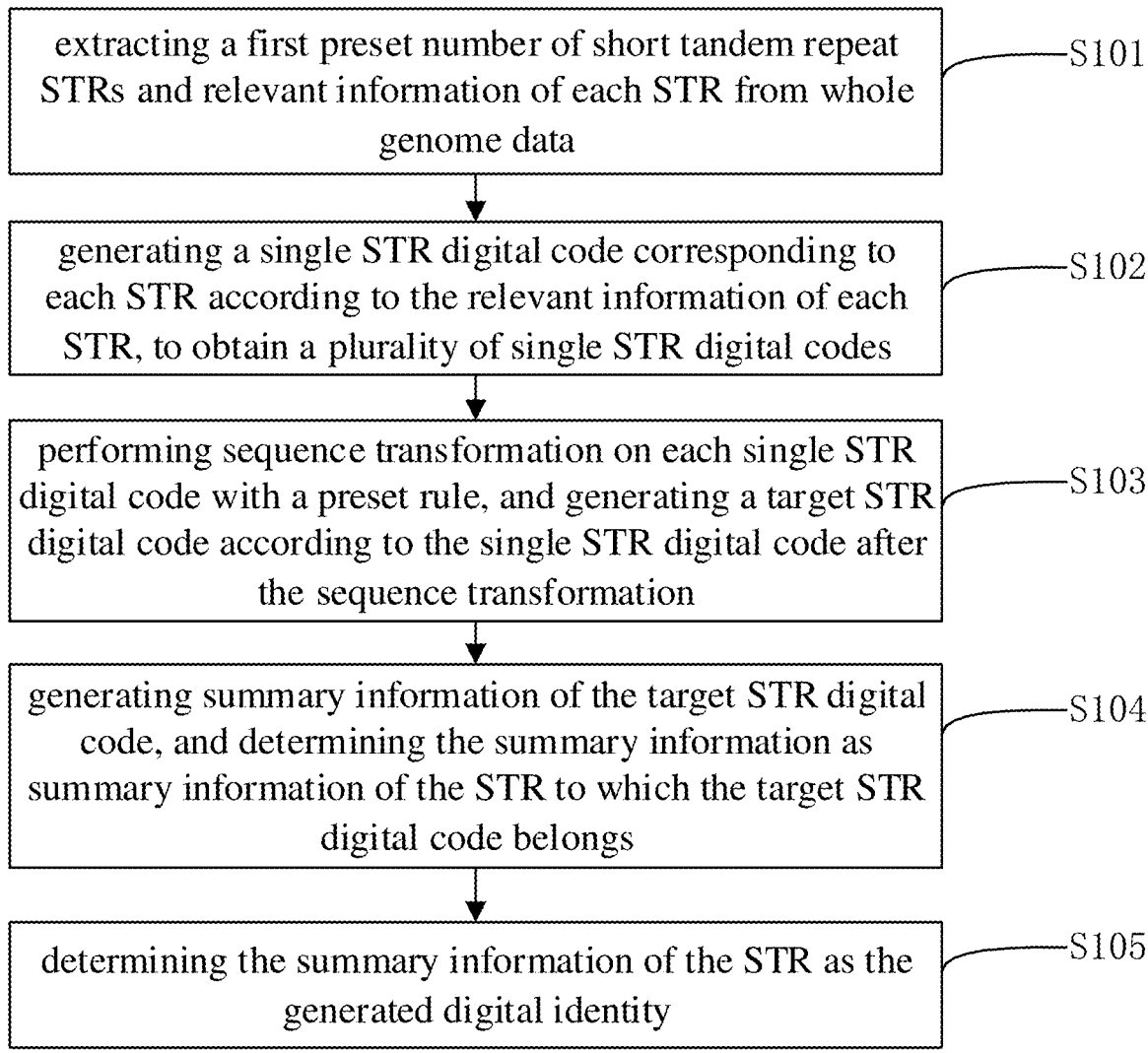
FIG. 1 is a schematic flowchart of a method for generating a digital identity proposed by an embodiment of the present application.
FIG. 2 is a schematic diagram of relevant information of each STR in an embodiment of the present application.

The embodiments of the present application are described in detail below. Examples of the embodiments are shown in the accompanying drawings, wherein the same or similar reference numerals represent the same or similar elements or elements with the same or similar functions. The embodiments described below with reference to the accompanying drawings are exemplary, and are only used to explain the present application, and cannot be understood as a limitation to the present application. On the contrary, the embodiments of the present application include all changes, modifications and equivalents falling within the scope of the spirit and connotation of the appended claims.

FIG. 1 is a schematic flowchart of a method for generating a digital identity according to an embodiment of the present application.

As an example, the method for generating the digital identity in this embodiment is configured for an apparatus for generating the digital identity.

The method for generating the digital identity in this embodiment may be configured for the apparatus for generating the digital identity. The apparatus may be set in a server or may also be set in an electronic device, which is not limited here.

As an example, the method for generating the digital identity in this embodiment is configured for an apparatus be set in an electronic device for generating the digital identity.

The digital identity therein is used to uniquely mark the identity information of a user and is generated based on the user's genome data. The electronic devices are hardware devices with various operating systems such as smart phones, tablet computers, personal digital assistants, e-books, smart wearable device such as smart bracelet, and the like.

It should be noted that the execution subject of the embodiments of the present application may be, for example, a central processing unit (CPU) of an electronic device in hardware, and may be, for example, an application in the electronic device for generating the digital identity in software, which is not limited here.

Traditional digital identities may be divided into two categories. One is the digital identity that needs to correspond to the physical identity with real names, which is referred to as entity digital identity for short. The most typical applications include resident ID cards issued by government, personal digital certificates issued by banks, and legal person digital certificates. The other is the virtual digital identity that does not need to correspond to the physical identity, which is referred to as virtual digital identity for short. Common applications include user names for a variety of network services, etc.

The corresponding relationship between the entity digital identity and the physical identity is as follows: the issuance and management of the entity digital identity require a real physical identity for associated authentication, that is, each digital identity corresponds to one real physical identity, and the physical identity is generally identified through the biometric information of a natural person (such as, facial features or fingerprint features).

The offline entity personal biometric information identification technology that the entity digital identity in related technologies relies on is relatively weak. Relying on biometric information identification technology to generate digital identities has the following problems: there is no guarantee for the uniqueness of biometrics without repetition in the digital identity application based on facial features identification technology (such as ID number), since the biometrics are of higher reproducibility (easier to perform a plastic surgery) and the accuracy of manual or machine facial identification cannot reach 100%. Thus the expression effect of digital identity is not good.

In order to solve the above technical problems, a method for generating a digital identity is provided by an embodiment of the present application, wherein the first preset number of short tandem repeat STRs and relevant information of each STR are extracted from whole genome data, the single STR digital code corresponding to each STR is generated according to the relevant information of each STR to obtain a plurality of single STR digital codes, sequence transformation is performed on each single STR digital code with a preset rule and the target STR digital code is generated according to the single STR digital code after the sequence transformation, summary information of the target STR digital code is generated and determined as summary information of the STR to which the target STR digital code belongs, and the summary information of the STR is determined as the generated digital identity. Since the digital identity is generated based on the STRs from whole genome data, the generated digital identity is unique and not easier to be copied. Further, since the digital encoding and sequence transformation is performed on the STR, the confidentiality and security of the generated digital identity may be effectively increased and the expression effect of the digital identity may also be enhanced.

Referring to FIG. 1, the method includes followings.

S101: a first preset number of short tandem repeat STRs and relevant information of each STR from whole genome data are extracted.

The whole genome data therein are currently needed to generate a digital identity of a user.

Based on the characteristics of genome data, there are N short tandem repeats (STR) in the whole genome data of a certain user. The STR is a short tandem repeat structure with a core sequence of 2-6 bases, in which a number of repetitions for the repeated base pairs sequence contained in each STR generally ranges from 1 to K. Based on the characteristics of genome data, the current value of N is greater than 7000 and the value of K is about 100. The number of repetitions for the repeated base pairs in the STR at a specific position on the chromosome is fixed for any specific user's whole genome data, but the number of repetitions at the same position may be different for different users, so polymorphism of STR is formed for the plurality of users. In the embodiment of the present application, a unique digital identity is generated based on polymorphic STR just due to the polymorphism of STR in the user's whole genome data and the digital identity may be used to uniquely express the identity of one user, so that the generated digital identity is unique and not easy to be copied.

In the embodiment of the present application, it provides a method in which massive different digital identities may be generated based on the polymorphism of STR. Each digital identity generated thereby is unique to this user and is not repeated with the digital identities of other users.

The whole genome data in the embodiment of the present application can be obtained from the published standard sequence of human genome Hg19.

As an example, the relevant information of each STR extracted in the embodiment of the present application may refer to FIG. 2, which is a schematic diagram of the relevant information of each STR in the embodiment of the present application. The relevant information of each STR is displayed in the form of a document, wherein each STR occupies a line, and the meanings of the content from left to right horizontally are as follows:

Score ID;
Perc div;
Perc del;
Perc ins;
Chromosome number;
start position of the query sequence;
stop position of the query sequence;
Sequence direction, where + is positive;
the repeated base sequence;
the type of the repeated sequence, where simple_repeat is STR;
start position of the repeated part;
stop position of the repeated part.

Figure 3:
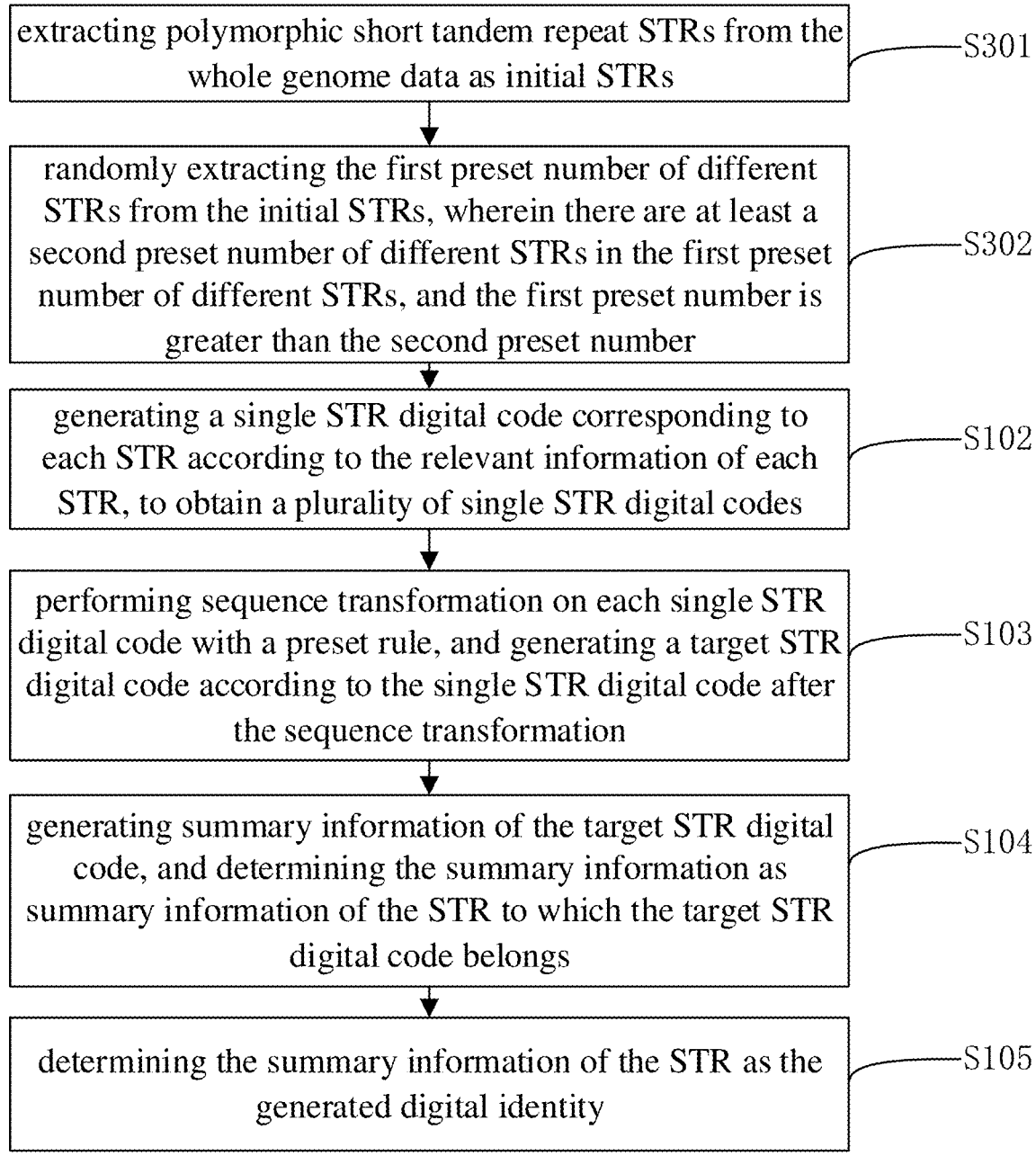
FIG. 3 is a schematic flowchart of a method for generating a digital identity according to another embodiment of the present application.

Alternatively, in some embodiments, referring to FIG. 3, the extracting the first preset number of short tandem repeat STRs from the whole genome data includes:

S301: polymorphic short tandem repeat STRs are extracted from the whole genome data as initial STRs.

S302: the first preset number of different STRs are randomly extracted from the initial STRs, wherein there are at least a second preset number of different STRs in the first preset number of different STRs, and the first preset number is greater than the second preset number.

The first preset number and the second preset number therein may be preset by the user according to usage requirements, or may also be preset by the factory program of the electronic device, which is not limited here.

The first preset number therein may be represented by M, and the second preset number may be represented by J.

In the specific implementation of the embodiment of the present application, in order to effectively make the generated digital identity unique, the polymorphic short tandem repeat STR may be extracted from the whole genome data as the initial STRs, so that the digital identity generated based on the user's whole genome data may be traced back to the unique biological identity, thereby effectively preventing identity fraud. The first preset number of different STRs randomly extracted each time may be used to generate a digital identity of the user. A plurality of random extraction mean that a plurality of different digital identities of the user may be generated and massive digital identities may also be generated, which may ensure that the same person uses different digital identities in each identification and ensure that the digital identity is not abused for occasions with high privacy protection.

In the specific implementation of the embodiment of the present application, in order to further ensure the uniqueness of the digital identity, at least a second preset number of different STRs may be configured in the first preset number of different STRs, wherein it is supposed that the first preset number M is about 50 and the second preset number J is about 30. In case that M is 50, the cumulative coincidence rate of the digital identities for two different users is lower than $10e^{-20}$, which is much higher than that of other biometric identification technologies in the related art.

In the specific implementation of the embodiment of the present application, the relevant information of M STRs may also be saved as index information. Referring to FIG. 4, FIG. 4 is a schematic diagram of index information in the embodiment of the present application, which facilitates the classification and storage of the relevant information of STR.

S102: a single STR digital code corresponding to each STR is generated according to the relevant information of each STR, to obtain a plurality of single STR digital codes.

Alternatively, in some embodiments, in order to technically realize the generation of a digital identity based on the relevant information of STR in the whole genome data, the single STR digital code may be configured to indicate position information and repeated base pair sequence information and a number of repetitions for the repeated base pairs sequence information of the corresponding STR in the whole genome data. Referring to FIG. 5, the generating the single STR digital code corresponding to each STR according to the relevant information of each STR, to obtain the plurality of single STR digital codes may include:

S501: the position information of each STR in the whole genome data is marked with a first number of bits, and the marked first number of bits is determined as a first digital code, the position information including chromosome number, a start position and a fragment length of the STR.

As an example, the first number in the embodiment of the present application is configured as 53, and the first number of bits is configured to mark the chromosome number, the start position and the fragment length of the STR, in which 5 bits may be configured to mark the chromosome number with binary; as for 24 chromosomes (chr1-chr22, chrx, chry) for example, the chromosome chr10 therein may be for example marked with 00010 and 40 bits may be configured to mark the start position with binary; 8 bits may be configured to mark the fragment length of the STR with binary, for example, the length of the repeating area of CCT fragment is 23, and the left end may be filled with 0000 to complete the number of bits.

In the specific implementation of the embodiment of the present application, considering that there are 24 types of human chromosomes (22 types of autosomes and 2 types of sex chromosomes), the smallest number of bits for the chromosome number is set as 5 in order to ensure subsequent actual development and update needs. The start position is set in a range of 1-109 and the smallest number of bits for the start position is set as 40. The fragment length of STR is set in a range of 1-600 and the smallest number of bits for the fragment length is set as 8.

An example is as follows:
Chr10→00010;
90608→0000000000000000000000010110000111110000;
23→00010111.

S502: the repeated base pair sequence information of each STR is marked with a second number of bits, and the marked second number of bits are determined as a second digital code.

The repeated base pair sequence information therein includes the content of the repeated base pair sequence of STR and the length of the repeated base pair sequence.

The second number in the embodiment of the present application is configured as 36. The 36 bits mark the content of the repeated base pair sequence of the STR, i.e., A is replaced by 100, G is replaced by 111, C is replaced by 110, T is replaced by 101, and the left end is filled with 0000 to complete the bits. The length of the repeated base pair sequence is in a range of 2-12. In the embodiment of the present application, the smallest number of bits is calculated as 12*3=36 based on the length of the longest base pair sequence and one base that may be replaced with a string of 3 bits.

An example is as follows:
CCT→000000000000000000000000000110110101.

S503: the number of repetitions for the repeated base pairs sequence is marked with a third number of bits, and the marked third number of bits is determined as a third digit code.

The third number in the embodiment of the present application is configured as 8. The 8 bits mark the number of repetitions for the repeated base pair sequence of the STR. The number of repetitions is less than or equal to K. The value of K is generally 50, which means that the number of repetitions is in a range of 2-50. As redundancy exceeding the upper limit may be reserved in the embodiment of the present application, the smallest number of bits is set as 8.

An example is described as follows:
5→400000101.

In the specific implementation of the embodiment of the present application, the repeated sequence of the corresponding position may be obtained through a program, and the number of repetitions may be determined.

S504: the first digital code, the second digital code and the third digital code of each STR are concatenated, and the concatenated digital code is determined as the single STR digital code corresponding to each STR.

In the specific implementation of the embodiment of the present application, the first digital code, the second digital code, and the third digital code may be concatenated to obtain the single STR digital code corresponding to this STR, such as STRECD=StartPosition |RepeatedSeq |RpeatedCnt) corresponding to the STR, its total length is 53+36+8=97 bits. The single STR digital code STRECD is then unified into an 8*S bit code by a method of filling the left end with sequence 1010.

In the embodiment of the present application, the first digital code, the second digital code and the third digital code of each STR are concatenated and the concatenated digital code is determined as the single STR digital code corresponding to each STR, so that the generated single STR digital code may completely mark the relevant information of the STR. The single STR digital code STRECD is unified into an 8*S bit code by a method of filling the left end with sequence 1010, which facilitates subsequent software processing.

An example is as follows: in case that the value of S is 16 in this implementation, the left end is filled with 31 bits to obtain:
1010101010101010101010101010101, A 128 bits binary sequence code is obtained, the specific value is as follows:
10110101010101010101010101010101010100010000000-00000000000000000101100001111100000000101110000-00000000000000000000011011010100000.

S103: sequence transformation is performed on each single STR digital code with a preset rule, and a target STR digital code is generated according to the single STR digital code after the sequence transformation.

In the embodiment of the present application, sequence transformation is performed on each single STR digital code with a preset rule, so that the target STR digital code generated according to the single STR digital code after the sequence transformation is unique.

In the specific implementation of the embodiment of the present application, sequence transformation is performed on each single STR digital code with a preset rule, and each single STR digital code after the sequence transformation is directly concatenated to obtain the concatenated STR digital codes, which may be referred as the target STR digital codes. The target STR digital codes correspond to the first preset number of short tandem repeat sequences STRs extracted in step S101. After a plurality of random extractions, one target STR digital code may be generated, wherein the target STR digital code corresponds to the first preset number of short tandem repeat sequences STRs extracted for each time.

Alternatively, as an example, the M STRECDs obtained from M STRs may be directly concatenated, to obtain a target STR digital code MSTRECD of the M STRs with a total bits of (8*S)*M.

S104: summary information of the target STR digital code is generated, and the summary information is determined as summary information of the STR to which the target STR digital code belongs.

Alternatively, a hash algorithm may be used to generate the summary information of the target STR digital code, so that the target STR digital code corresponds to the unique summary information.

In the specific implementation of the embodiment of the present application, a hash algorithm may be used to perform summary calculation on the target STR digital code MSTRECD to obtain a calculation result, and generate HASH summary with F bits corresponding to the calculation result as summary information of the target STR digital code.

In the embodiment of the present application, the value of F may be greater than or equal to 256 and common values are, for example, 256, 512, or 1024.

Hash algorithms include SHA256 and SHA512, for example.

In the embodiment of the application, summary information of the target STR digital code is generated, and the summary information is determined as summary information of the STR to which the target STR digital code belongs; each different target STR digital code may be mapped as a binary sequence with a different content and a fixed length of F via the transformation and the target STR digital code may not be restored through the binary sequence, thereby ensuring the confidentiality and security of the digital identity.

An example of summary information of the STR to which the target STR digital code belongs is as follows:
570EA6E6A236C6E48B482FAA4F9BDD6BD223258-41D3ACF69A88CE08843C0143A.

S105: the summary information of the STR is determined as the generated digital identity.

In the embodiment of the present application, the summary information of the STR may be used as a digital identity that may be used to uniquely identify the user. Based on the same genome data, a large number of complementary and identical digital identities may be generated.

In the embodiment of the present application, the value of the first preset number M may ensure that the digital identities generated by any two different users are different. The value of M may be configured to be greater than or equal to 50 in the embodiment of the present application. The value of J is configured to ensure that the generated digital identity of the same user for each time is different. In this embodiment of the present application, the value range of J may be configured as M≥J≥30.

An examples is described as follows:
In case that there are N short tandem repeat sequences STRs in which the value of N is 7000, the value of M is 50 and the value of J is 30, the number of digital identities that may be generated according to the method in the embodiment of the present application is approximately equal to the data that are obtained by the following equation:

$$\frac{N!}{(N-M)!} = \frac{7000!}{(7000-50)!};$$

The result is about $5 \times e^{150}$ orders of magnitude.

Figure 6:
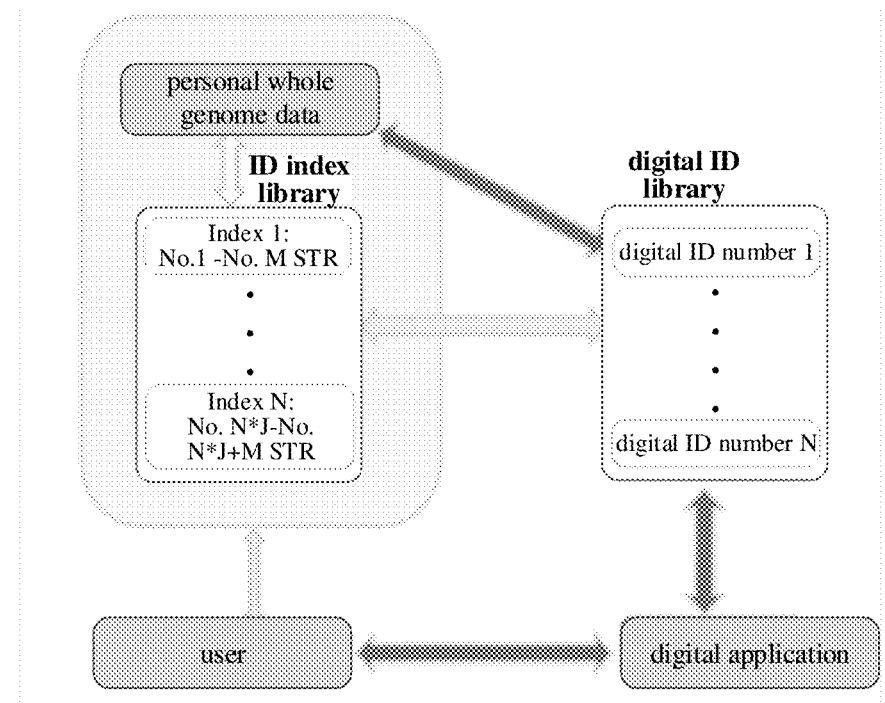
FIG. 6 is a schematic diagram of a digital identity ID database in an embodiment of the present application.

Further, the digital identity generated according to the method in the embodiment of the present application may be used for identification in digital application technology. A typical application scenario is described as follows:

1. User digital identity ID database: According to the digital identity generated by the method in the embodiment of the present application, a large number of different digital identities may be generated for each user, which may be for use in a digital identity ID database as shown in FIG. 6. FIG. 6 is a schematic diagram of the digital identity ID database in the embodiment of the present application, which is different from an application scenario where the user's digital identity is fixed in network applications in the related art. The user may perform application operations with a different digital identity for each time in the digital system, thereby improving the security of the user's application of the digital system. In addition, combined with a third-party service system, the used digital identity may be invalidated to prevent subsequent fraudulent use by other users.

2. Digital identification: The digital identity generated according to the method in the embodiment of the present application has a high security. The user may accurately verify the real correspondence between the current number and the user by virtue of the whole genome data and index information corresponding to the digital identity.

3. User identification in the blockchain system: user information in the blockchain system requires a separate ID number for identification. The digital identity generated according to the method in the embodiment of the present application is used as the user information ID for each time, which may improve the ID security.

4. Transaction information identification in the blockchain system: each transaction in the blockchain system requires a separate ID number for identification. As a transaction ID, the digital identity generated according to the method in the embodiment of the present application may enhance privacy protection. Specifically, a transaction initiated by the same user uses its different digital identity as the transaction ID. After the transaction is stored on the chain, only the user may verify whether the transaction ID was initiated by himself/herself through the user digital identity ID database.

In this embodiment, the first preset number of short tandem repeat STRs and relevant information of each STR are extracted from whole genome data, the single STR digital code corresponding to each STR is generated according to the relevant information of each STR to obtain a plurality of single STR digital codes, sequence transformation is performed on each single STR digital code with a preset rule and the target STR digital code is generated according to the single STR digital code after the sequence transformation, summary information of the target STR digital code is generated and determined as summary information of the STR to which the target STR digital code belongs, and the summary information of the STR is determined as the generated digital identity. Since the digital identity is generated based on the STRs from whole genome data, the generated digital identity is unique and not easier to be copied. Further, since the digital encoding and sequence transformation is performed on the STR, the confidentiality and security of the generated digital identity may be effectively increased and the expression effect of the digital identity may also be enhanced.

As an example, a specific example of a method for generating a digital identity in the embodiment of the present invention is as follows:

1. polymorphic short tandem repeat STRs are extracted from the whole genome data as initial STRs.

2. the first preset number of different STRs are randomly extracted from the initial STRs, wherein there are at least a second preset number of different STRs in the first preset number of different STRs, and the first preset number is greater than the second preset number.

at least a second preset number of different STRs may be configured in the first preset number of different STRs, wherein it is supposed that the first preset number M is about 50 and the second preset number J is about 30. In case that M is 50, the cumulative coincidence rate of the digital identities for two different users is lower than $10e^{-20}$, which is much higher than that of other biometric identification technologies in the related art.

3. the relevant information of each STR is extracted.

The relevant information of each STR extracted in the embodiment of the present application may refer to FIG. 2, which is a schematic diagram of the relevant information of each STR in the embodiment of the present application. The relevant information of each STR is displayed in the form of a document, wherein each STR occupies a line, and the meanings of the content from left to right horizontally are as follows:

Score ID;
Perc div;
Perc del;
Perc ins;
Chromosome number;
start position of the query sequence;
stop position of the query sequence;
Sequence direction, where + is positive;
the repeated base sequence;
the type of the repeated sequence, where simple_repeat is STR;
start position of the repeated part;
stop position of the repeated part.

4. the position information of each STR in the whole genome data is marked with a first number of bits, and the marked first number of bits is determined as a first digital code, the position information including chromosome number, a start position and a fragment length of the STR.

As an example, the first number in the embodiment of the present application is configured as 53, and the first number of bits is configured to mark the chromosome number, the start position and the fragment length of the STR, in which 5 bits may be configured to mark the chromosome number with binary; as for 24 chromosomes (chr1-chr22, chrx, chry) for example, the chromosome chr10 therein may be for example marked with 00010 and 40 bits may be configured to mark the start position with binary; 8 bits may be configured to mark the fragment length of the STR with binary, for example, the length of the repeating area of CCT fragment is 23, and the left end may be filled with 0000 to complete the number of bits.

In the specific implementation of the embodiment of the present application, considering that there are 24 types of human chromosomes (22 types of autosomes and 2 types of sex chromosomes), the smallest number of bits for the chromosome number is set as 5 in order to ensure subsequent actual development and update needs. The start position is set in a range of 1-109 and the smallest number of bits for the start position is set as 40. The fragment length of STR is set in a range of 1-600 and the smallest number of bits for the fragment length is set as 8.

An examples is as follows:

Chr10→00010;

90608→000000000000000000000000101100001111100-00;

23→00010111.

5. the repeated base pair sequence information of each STR is marked with a second number of bits, and the marked second number of bits are determined as a second digital code.

The repeated base pair sequence information therein includes the content of the repeated base pair sequence of STR and the length of the repeated base pair sequence.

The second number in the embodiment of the present application is configured as 36. The 36 bits mark the content of the repeated base pair sequence of the STR, i.e., A is replaced by 100, G is replaced by 111, C is replaced by 110, T is replaced by 101, and the left end is filled with 0000 to complete the bits. The length of the repeated base pair sequence is in a range of 2-12. In the embodiment of the present application, the smallest number of bits is calculated as 12*3=36 based on the length of the longest base pair sequence and one base that may be replaced with a string of 3 bits.

An examples is as follows:
CCT→000000000000000000000000000110110101.

6. the number of repetitions for the repeated base pairs sequence is marked with a third number of bits, and the marked third number of bits is determined as a third digit code.

The third number in the embodiment of the present application is configured as 8. The 8 bits mark the number of repetitions for the repeated base pair sequence of the STR. The number of repetitions is less than or equal to K. The value of K is generally 50, which means that the number of repetitions is in a range of 2-50. As redundancy exceeding the upper limit may be reserved in the embodiment of the present application, the smallest number of bits is set as 8.

An examples is as follows:

5→00000101.

7. the first digital code, the second digital code and the third digital code of each STR are concatenated, and the concatenated digital code is determined as the single STR digital code corresponding to each STR.

In the specific implementation of the embodiment of the present application, the first digital code, the second digital code, and the third digital code may be concatenated to obtain the single STR digital code corresponding to this STR, such as STRECD=StartPosition |RepeatedSeq |RpeatedCnt) corresponding to the STR, its total length is 53+36+8=97 bits. The single STR digital code STRECD is then unified into an 8*S bit code by a method of filling the left end with sequence 1010.

An example is as follows: in case that the value of S is 16 in this implementation, the left end is filled with 31 bits to obtain:

10101010101010101010101010101,

A 128 bits binary sequence code is obtained, the specific value is as follows:

10110101010101010101010101010101000100000000000000000000000001011000011111
0000000101110000000000000000000000000000011011010100000.

8. sequence transformation is performed on each single STR digital code with a preset rule, and a target STR digital code is generated according to the single STR digital code after the sequence transformation.

As an example, the M STRECDs obtained from M STRs may be directly concatenated, to obtain a target STR digital code MSTRECD of the M STRs with a total bits of (8*S)*M.

An example of the target STR digital code MSTRECD is as follows:

10110101010101010101010101010101000100000000000000000000000001010000011111
00000001011100000000000000000000000000000110110101000010110101010101010101010101
01010101000100000000000000000000010010000111110000000101110000000000000110110
10100000101101010101010101010101010101010100010000000000000000000000101100001
11110000000010100000000000010011010110000101101010101010101010101010101010001000
10000000000000000000000101110001111100000000111100000000000011011010100001011
01010101010101010101010101010101000100000000000000000000000010110000111110000001
01110000000000000000000000000000011011010100000101101010101010101010101010101010
00010000000111110000000010111000000000000110110101000000
10110101010101010101010101010101000100000000000000000000000010010000111110000
000101110000000000110110101000010110101010101010101010101010101010100010000000
00000000000000000010110010011000000010100000000000100110101110001011010101010
10101010101010101010101000100000000000000000000000110110001111100000000111100000
00000001101101010000010110101000010110101010101010101010101010101010100010000000000000
0000010110001111000000001011100000000000001011010110001011010101010101010101010101
010101010100010000001111100000001010000000000000110101000000101010000010110101010101010101010101010101010101000010000000000000000000000101100011111000000001010100000000000001

```
0011010110000101101010101010101010101010101010001000000000000000000000001011
1000111110000000111010000000000001101101010000101101010101010101010101010
1000010000000000000000000000001011000011110000000110110000000000001101101010000
1011010101010101010101010101010001000000000000000000000000010100000101110000
0000000000000000101110000000000001101101010000010110101010101010101010101010
1000100000000000000000000010010000011100000000101110000000000001101101010000
0101101010101010101010101010100010000000000000000000000010110000100110000
0000101010000000000100110101100010110101010101010101010101010100010000000
0000000000000000011000000111100000001111000000000000001101101010000010110101010
1010101010101010101010100010000000000000000000001011000011100000000101110000
0000000000000000101101011000010110101010101010101010101010100010000
0000000000000000010000001111000000010111000000000000110110101000001011010101
0101010101010101010100010000000000000000010000111110000000101111
000000000011011010100000101101010101010101010101010101010001000000000000000
00000000010110000111100000001010000000000000100110101100010110101010101010
1010101010101000100000000000000000000000000000000101110001111000000001111000000000000
1101101010000010110101010101010101010101010101010000000000000000000000000101
1000011110000000101110000000000001101101010000010110101010101010101010101010101
0100010000000000000000000000010100000111010000000010110000000000001101101010000
001011010101010101010101010100010000000000000000000000000100100001101100
0000110111000000000000011011010100000101101010101010101010101010101010001000100000
000000000000000010110000100110000001010000000000001001101011000101101010
1010101010101010101000100010000000000000000000001011000111100000000111110
0000000000011011010100000101101010101010101010101010101000010000000000000000
000000010110000111100000000010001000000000000000110010101100010110101010101010101
10101010101010010001000011110000001011100000000101100000000000001
10110101000001011010101010101010101010101010001000000000000000000
0000111100000000101100000000000110110101000001011010101010101010101010101010
100010000000000000000000001011000011110000000101010000000000010011010110000
010110101010101010101010101010100010111001111100000000000011011010
10000010110101010101010101010101010101010001000000000011100000010111000
0000000110110101000001011010101010101010101010101010100001000000001000000010111000
0000100100001111000000000010111000000000001101111010000010110101010101010101010
1010101010100010000000000000000000000000101100001001000000001010000000000000100
11010111000101101010101010101010101010101010001000000000000000000000001111110
0011111000000011111000000000000010110101000001011010101010101010101010101010
000100000000000000000000000101100001111000000010111000000000000101101011000001
0110101010101010101010101010000100000000000000000000000101000000111110000
001011100000000000011011010100000101101010101010101010101010100010000000100000000
00000000000000001001000011110000000101110000000000001101101010000010110101010
10101010101010101010100010000000000000000000000000010110000111100000001010100000
00000000100110101100001011010101010101010101010101010001001101011000101101010
10101010101010101000100000000000000000000000000101100001111000000011110
00000000000001101101010000010110101010101010101010101010101010100010000000000
00000000001011000011110000000101010000000000001001101011000101101010101010101010
1010101010001000000000000001011000011110000000010100000000000001011011000001
0110101010101010101010101010100010000010110110001011010101010101010101010101010100010000010111000
000000010011010110001011010101010101010101010101010101000100000000000000000000
000001011000111100000001111000000000000110110101000010110101010101010101010101010
10101000100000000000000000000000000011100001111000000001011100000000000101
01100001111000000010111000000000001101101100001011010101010101010101010101010
0101010000010110000011110000000111000000000000011101100001011010101010101010101
0100101010101010001000000000000000000000010110001111000000010111000000000001
101101010000010110101010101010101010101010101010000000101100011110000000101110000000
00000110110101000001011010101010101010101010101010000010110000000000000000
0000010110001111000000010110000000000001101101010000101101010101010101010101010
101010101010001000000000000001011000011110000000010010100000000100110101
100010110101010101010101010101010101000010001000000000000000000000000101100001111
1000000100110000000000110110101000001011010101010101010101010101010101010001000100
0000000001011000111100000010111000000000000011011101100001011010101010101010101010
10101010100000101110010101101010101010101010101010101010000100010000000000
10101010101010101010100010000000000000000000000101100011111000000010110000000000
1011000011110000000101110000000000011011010100000.
```

9. A hash algorithm is used to generate the summary information of the target STR digital code, so that the target STR digital code corresponds to the unique summary information.

An example of summary information of the STR to which the target STR digital code belongs is as follows:

570EA6E6A236C6E48B482FAA4F9BDD6BD223258-41D3ACF69A88CE08843C0143A.

10. the summary information of the STR is determined as the generated digital identity.

In the embodiment of the present application, the value of the first preset number M may ensure that the digital identities generated by any two different users are different. The value of M may be configured to be greater than or equal to 50 in the embodiment of the present application. The value of J is configured to ensure that the generated digital identity of the same user for each time is different. In this embodiment of the present application, the value range of J may be configured as M≥J≥30.

An examples is described as follows:

In case that there are N short tandem repeat sequences STRs in which the value of N is 7000, the value of M is 50 and the value of J is 30, the number of digital identities that may be generated according to the method in the embodiment of the present application is approximately equal to the data that are obtained by the following equation:

$$\frac{N!}{(N-M)!} = \frac{7000!}{(7000-50)!};$$

The result is about $5 \times e^{150}$ orders of magnitude.

Figure 7:
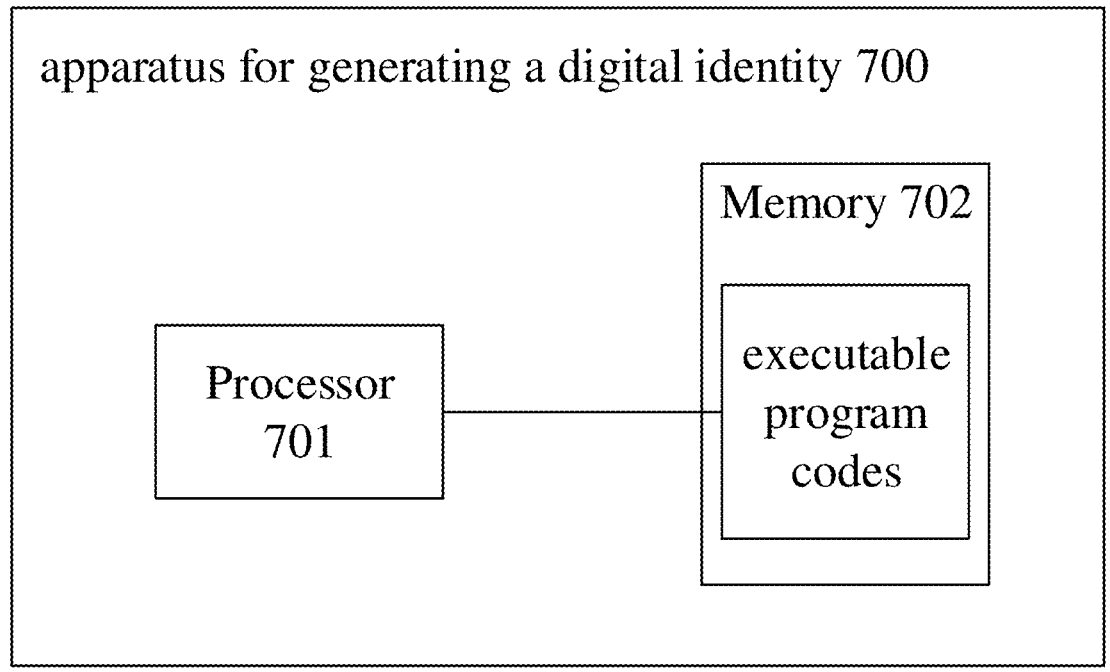
FIG. 7 is a structural schematic diagram of an apparatus for generating a digital identity according to an embodiment of the present application.

FIG. 7 is a structural schematic diagram of apparatus for generating a digital identity according to an embodiment of the present application.

Referring to FIG. 7, the apparatus 700 includes: a processor 701; a memory 702; the memory 702 stores executable program code. The processor 701 is configured to execute programs corresponding to the executable program codes by reading the executable program codes stored in the memory 702, so as to perform:

extracting a first preset number of short tandem repeat STRs and relevant information of each STR from whole genome data;

generating a single STR digital code corresponding to each STR according to the relevant information of each STR, to obtain a plurality of single STR digital codes;

performing sequence transformation on each single STR digital code with a preset rule, and generating a target STR digital code according to the single STR digital code after the sequence transformation;

generating summary information of the target STR digital code, and determining the summary information as summary information of the STR to which the target STR digital code belongs; and determining the summary information of the STR as the generated digital identity.

Alternatively, in some embodiments, the processor 701 is further configured to:

extract the polymorphic short tandem repeat STRs from the whole genome data as initial STRs; and randomly extract the first preset number of different STRs from the initial STRs, wherein there are at least a second preset number of different STRs in the first preset number of different STRs, and the first preset number is greater than the second preset number.

Alternatively, in some embodiments, the single STR digital code is configured to indicate position information of the corresponding STR in the whole genome data, repeated base pair sequence information and a number of repetitions for the repeated base pairs sequence. The processor 701 is further configured to:

mark the position information of each STR in the whole genome data with a first number of bits, and determining the marked first number of bits as a first digital code, the position information comprising chromosome number, a start position and a fragment length of the STR;

mark the repeated base pair sequence information of each STR with a second number of bits, and determining the marked second number of bits as a second digital code;

mark the number of repetitions for the repeated base pairs sequence with a third number of bits, and determining the marked third number of bits as a third digit code; and perform concatenation processing on the first digital code, the second digital code, and the third digital code of each STR, and determining the concatenated digital code as the single STR digital code corresponding to each STR.

Alternatively, in some embodiments, the processor 701 is further configured to:

make the target STR digital code generated according to the single STR digital code after the sequence transformation unique.

Alternatively, in some embodiments, the processor 701 is further configured to:

generate the summary information of the target STR digital code by a hash algorithm, so that the target STR digital code corresponds to one unique summary information.

It should be noted that the explanations of the embodiments of the method for generating a digital identity in the aforementioned embodiments from FIG. 1 to FIG. 6 are also applicable to the apparatus 700 for generating a digital identity of this embodiment. The implementation principle for the apparatus is similar with that for the method, which will not be repeated here.

In this embodiment, the first preset number of short tandem repeat STRs and relevant information of each STR are extracted from whole genome data, the single STR digital code corresponding to each STR is generated according to the relevant information of each STR to obtain a plurality of single STR digital codes, sequence transformation is performed on each single STR digital code with a preset rule and the target STR digital code is generated according to the single STR digital code after the sequence transformation, summary information of the target STR digital code is generated and determined as summary information of the STR to which the target STR digital code belongs, and the summary information of the STR is determined as the generated digital identity. Since the digital identity is generated based on the STRs from whole genome data, the generated digital identity is unique and not easier to be copied. Further, since the digital encoding and sequence transformation is performed on the STR, the confidentiality and security of the generated digital identity may be effectively increased and the expression effect of the digital identity may also be enhanced.

In order to implement the above embodiments, the present application also provides a non-transitory computer-readable storage medium which is configured to store application programs. The application programs are configured to perform a method for generating the digital identity of the embodiment of the present application. The method includes:

extracting a first preset number of short tandem repeat STRs and relevant information of each STR from whole genome data;

generating a single STR digital code corresponding to each STR according to the relevant information of each STR, to obtain a plurality of single STR digital codes;

performing sequence transformation on each single STR digital code with a preset rule, and generating a target STR digital code according to the single STR digital code after the sequence transformation;

generating summary information of the target STR digital code, and determining the summary information as summary information of the STR to which the target STR digital code belongs; and determining the summary information of the STR as the generated digital identity.

It should be noted that the principle and implementation of performing by application programs the method for generating the digital identity in this embodiment are similar to those of the method for generating the digital identity in the above embodiment. In order to avoid redundancy, the details are not repeated here.

Through the non-transitory computer-readable storage medium in the embodiment of the present application, the first preset number of short tandem repeat STRs and relevant information of each STR are extracted from whole genome data, the single STR digital code corresponding to each STR is generated according to the relevant information of each STR to obtain a plurality of single STR digital codes, sequence transformation is performed on each single STR digital code with a preset rule and the target STR digital code is generated according to the single STR digital code after the sequence transformation, summary information of the target STR digital code is generated and determined as summary information of the STR to which the target STR digital code belongs, and the summary information of the STR is determined as the generated digital identity. Since the digital identity is generated based on the STRs from whole genome data, the generated digital identity is unique and not easier to be copied. Further, since the digital encoding and sequence transformation is performed on the STR, the confidentiality and security of the generated digital identity may be effectively increased and the expression effect of the digital identity may also be enhanced.

It should be noted that in the descriptions of the present application, the terms "first", "second", etc. are only used for descriptive purposes, and may not be understood as indicating or implying relative importance. In addition, in the descriptions of the present application, unless otherwise specified, "a plurality of" means two or more.

Any process or method description in the flowchart or described in other ways herein may be understood as a module, a segment or a part of codes that include one or more executable instructions for implementing specific logical functions or steps of the process. And the scope of the preferred embodiments of the present application includes additional implementations, which may not be in an order as shown or discussed, including performing functions in a substantially simultaneous manner or in a reverse order according to the functions involved, which should be understood by those skilled in the art to which the embodiments of the present application belong.

It should be understood that each part of the present application may be implemented in hardware, software, firmware or a combination thereof. In the above embodiments, multiple steps or methods may be implemented in software or firmware stored in a memory and executed by a suitable instruction execution system. For example, if it is implemented in hardware, as in another embodiment, it may be implemented by any one or a combination of the following technologies known in the art: discrete logic circuits of logic gate circuits for implementing logic functions on data signals, application-specific integrated circuits with suitable combinational logic gates, programmable gate arrays (PGA), field programmable gate arrays (FPGA), etc.

Those skilled in the art may understand that all or part of the steps carried in the method of the above embodiments may be implemented by a program instructing relevant hardware to complete. The program may be stored in a computer-readable storage medium. When executed, it includes one of the steps of the method embodiment or a combination thereof.

In addition, various functional units in various embodiments of the present application may be integrated into one processing module, or each unit may exist alone physically, or two or more units may be integrated into one module. The above-mentioned integrated modules may be implemented in the form of hardware or software functional modules. If the integrated module is implemented in the form of software function modules and sold or used as an independent product, it may also be stored in a computer readable storage medium.

The storage medium mentioned above may be a read-only memory, a magnetic disk or an optical disk, etc.

In the description of this specification, descriptions with reference to the terms "one embodiment", "some embodiments", "examples", "specific examples", or "some examples" etc. mean specific features, structures, materials, or characteristics described in conjunction with the embodiment or example are included in at least one embodiment or example of the present application. In this specification, the schematic representations of the above terms do not necessarily refer to the same embodiment or example. Moreover, the specific features, structures, materials or characteristics as described may be combined in any one or more embodiments or examples in a suitable manner.

Although the embodiments of the present application have been shown and described above, it may be understood that the above embodiments are exemplary and should not be construed as limiting the present application. those skilled in the art may make changes, modifications, replacements and modifications on the above embodiments within the scope of the present application.

What is claimed is:

1. A method for generating a digital identity, comprising the following acts performed by a digital identity generating device:

extracting a first preset number of short tandem repeats (STRs) and relevant information of each STR from whole genome data;

generating a single STR digital code corresponding to each STR according to the relevant information of each STR, to obtain a plurality of single STR digital codes;

performing sequence transformation on each single STR digital code with a preset rule, and generating a target STR digital code according to the single STR digital code after the sequence transformation;

generating summary information of the target STR digital code, and determining the summary information as summary information of the STR to which the target STR digital code belongs; and determining the summary information of the STR as the generated digital identity, wherein the extracting the first preset number of STRs and the relevant information of each STR from whole genome data, comprises:

extracting polymorphic short tandem repeats STRs from the whole genome data as initial STRs; and randomly extracting the first preset number of different STRs from the initial STRs, wherein there are at least a second preset number of different STRs in the first preset number of different STRs, and the first preset number is greater than the second preset number.

2. The method according to claim 1, wherein the single STR digital code is configured to indicate position information in the whole genome data, repeated base pair sequence information and a number of repetitions for the repeated base pairs sequence of the corresponding STR, and the generating the single STR digital code corresponding to each STR according to the relevant information of each STR, to obtain the plurality of single STR digital codes comprises:

marking the position information of each STR in the whole genome data with a first number of bits, and determining the marked first number of bits as a first digital code, the position information comprising chromosome number, a start position and a fragment length of the STR;

marking the repeated base pair sequence information of each STR with a second number of bits, and determining the marked second number of bits as a second digital code;

marking the number of repetitions for the repeated base pairs sequence with a third number of bits, and determining the marked third number of bits as a third digit code; and performing concatenation processing on the first digital code, the second digital code, and the third digital code of each STR, and determining the concatenated digital code as the single STR digital code corresponding to each STR.

3. The method according to claim 1, wherein,
the target STR digital code generated according to the single STR digital code after the sequence transformation is unique.

4. The method according to claim 1, wherein the generating summary information of the target STR digital code, and determining the summary information as summary information of the STR to which the target STR digital code belongs, comprise:

generating the summary information of the target STR digital code by a hash algorithm, so that the target STR digital code corresponds to one unique summary information.

5. An apparatus for generating a digital identity, comprising:
a processor; and
a memory storing executable program codes,
wherein the processor is configured to execute programs corresponding to the executable program codes by reading the executable program codes stored in the memory, so as to perform:

extracting a first preset number of short tandem repeats (STRs) and relevant information of each STR from whole genome data;

generating a single STR digital code corresponding to each STR according to the relevant information of each STR, to obtain a plurality of single STR digital codes;

performing sequence transformation on each single STR digital code with a preset rule, and generating a target STR digital code according to the single STR digital code after the sequence transformation;

generating summary information of the target STR digital code, and determining the summary information as summary information of the STR to which the target STR digital code belongs;

determining the summary information of the STR as the generated digital identity, wherein the extracting the first preset number of STRs and the relevant information of each STR from whole genome data, comprises:

extracting polymorphic short tandem repeats STRs from the whole genome data as initial STRs;

randomly extracting the first preset number of different STRs from the initial STRs, wherein there are at least a second preset number of different STRs in the first preset number of different STRs, and the first preset number is greater than the second preset number.

6. The apparatus according to claim 5, wherein the single STR digital code is configured to indicate position information of the corresponding STR in the whole genome data, repeated base pair sequence information and a number of repetitions for the repeated base pairs sequence, and the processor is further configured to:

mark the position information of each STR in the whole genome data with a first number of bits, and determine the marked first number of bits as a first digital code, the position information comprising chromosome number, a start position and a fragment length of the STR;

mark the repeated base pair sequence information of each STR with a second number of bits, and determine the marked second number of bits as a second digital code;

mark the number of repetitions for the repeated base pairs sequence with a third number of bits, and determine the marked third number of bits as a third digit code;

perform concatenation processing on the first digital code, the second digital code, and the third digital code of each STR, and use the concatenated digital code as the single STR digital code corresponding to each STR.

7. The apparatus according to claim 5, wherein:
the target STR digital code generated according to the single STR digital code after the sequence transformation is unique.

8. The apparatus for generating the digital identity according to claim 5, wherein the processor is further configured to:

generate the summary information of the target STR digital code by a hash algorithm, so that the target STR digital code corresponds to one unique summary information.

9. A non-transitory computer-readable storage medium having instructions stored therein, wherein when the instructions are executed by a processor of an electronic device, the processor is configured to perform a method for generating a digital identity, and the method comprises:

extracting a first preset number of short tandem repeats (STRs) and relevant information of each STR from whole genome data;

generating a single STR digital code corresponding to each STR according to the relevant information of each STR, to obtain a plurality of single STR digital codes;

performing sequence transformation on each single STR digital code with a preset rule, and generating a target STR digital code according to the single STR digital code after the sequence transformation;

generating summary information of the target STR digital code, and determining the summary information as summary information of the STR to which the target STR digital code belongs; and determining the summary information of the STR as the generated digital identity, wherein the extracting the first preset number of STRs and the relevant information of each STR from whole genome data, comprises:

extracting polymorphic short tandem repeats STRs from the whole genome data as initial STRs; and randomly extracting the first preset number of different STRs from the initial STRs, wherein there are at least a second preset number of different STRs in the first preset number of different STRs, and the first preset number is greater than the second preset number.

* * * * *